(12) United States Patent
Bray

(10) Patent No.: US 7,652,189 B2
(45) Date of Patent: Jan. 26, 2010

(54) CARBOXYMETHYLATED CELLULOSIC WOUND DRESSING

(75) Inventor: Roger Bray, Whitestone (GB)

(73) Assignee: ConvaTec Limited, Deeside, Flintshire (GB)

( * ) Notice: Subject to any disclaimer, the term of this patent is extended or adjusted under 35 U.S.C. 154(b) by 784 days.

(21) Appl. No.: 10/513,065

(22) PCT Filed: May 2, 2003

(86) PCT No.: PCT/GB03/01926

§ 371 (c)(1),
(2), (4) Date: Jun. 29, 2005

(87) PCT Pub. No.: WO03/092755

PCT Pub. Date: Nov. 13, 2003

(65) Prior Publication Data

US 2005/0272331 A1     Dec. 8, 2005

(30) Foreign Application Priority Data

May 3, 2002    (GB) ................... 0210233.3

(51) Int. Cl.
*A61F 5/00*      (2006.01)
*A61F 13/00*    (2006.01)
*A61F 13/06*    (2006.01)
*B32B 3/10*      (2006.01)
*D01F 9/12*      (2006.01)

(52) U.S. Cl. .................. 602/44; 602/41; 602/42; 602/43; 602/60; 602/61; 128/898; 428/139; 423/447.1

(58) Field of Classification Search ............. 602/41–44, 602/60–61; 128/898; 428/139; 423/447.1
See application file for complete search history.

(56) References Cited

U.S. PATENT DOCUMENTS

| | | | | |
|---|---|---|---|---|
| 3,723,413 | A * | 3/1973 | Chatterjee et al. | 536/87 |
| 4,405,324 | A * | 9/1983 | Cruz, Jr. | 604/376 |
| 4,579,943 | A * | 4/1986 | Kamide et al. | 536/98 |
| 5,731,083 | A * | 3/1998 | Bahia et al. | 428/393 |
| 6,075,177 | A * | 6/2000 | Bahia et al. | 602/43 |
| 6,548,730 | B1 * | 4/2003 | Patel et al. | 602/56 |
| 2002/0099318 | A1 * | 7/2002 | Suehr et al. | 602/76 |
| 2005/0061204 | A1 * | 3/2005 | Skuratowicz | 106/162.5 |
| 2005/0148920 | A1 * | 7/2005 | Addison | 602/46 |
| 2007/0042024 | A1 * | 2/2007 | Gladman et al. | 424/445 |
| 2007/0042025 | A1 * | 2/2007 | Gladman et al. | 424/445 |

FOREIGN PATENT DOCUMENTS

| | | |
|---|---|---|
| GB | 2357286 | 6/2001 |
| WO | WO 00/01425 | 1/2000 |

* cited by examiner

*Primary Examiner*—Patricia M Bianco
*Assistant Examiner*—Brandon Jackson
(74) *Attorney, Agent, or Firm*—John M. Kilcoyne

(57) ABSTRACT

Wound dressings in the form of a body-shaped component are composed of body-shaped cellulosic fabric which has been carboxymethylated at the woundcontacting surface. The body-shaped component composed of a fabric comprising a cellulosic material is subjected to a carboxymethylation process to carboxymethylate the cellulosic material at the wound-contacting surface.

13 Claims, No Drawings

CARBOXYMETHYLATED CELLULOSIC WOUND DRESSING

FIELD OF THE INVENTION

This invention relates to wound dressings of the type in which the wound-contacting surface is composed of a cellulosic material that has been subjected to carboxymethylation.

BACKGROUND ART

It is known to use carboxymethylated cellulosic materials in situations where a high degree of moisture absorbency is required. For example, WO93/12275 describes the production of various absorbent products such as disposable nappies (diapers), tampons, sanitary napkins, incontinence pads and the like. The advantage of carboxymethylated cellulosic materials, for example the carboxymethylated solvent-spun cellulose (lyocell) material to which WO93/12275 is particularly directed, is that they are capable of absorbing many times their own weight of water or aqueous fluid. This causes the carboxymethylated fibres to form a gel, which effectively serves to entrap the absorbed moisture.

One application in which absorption of moisture is of importance is the dressing of wounds, particularly exuding wounds. Carboxymethylated lyocell materials have been successfully utilised in wound dressing materials, and their use for this purpose is described, for example, in WO94/16746 and WO00/01425. The gel-forming characteristic of such materials is of particular advantage in the treatment of wounds, since the gel tends to prevent adherence and therefore minimises the wound damage and pain which can often occur when a wound dressing is removed. The attention of the reader is directed to the full disclosures of these documents for a fuller discussion of the preferred degree of carboxymethylation to achieve optimal results, and of the reaction conditions by means of which carboxymethylation may advantageously be achieved in practice.

The techniques described in these documents have resulted in commercially successful wound dressings, which are essentially flat but flexible, for example rectangular, circular or of some other planar shape and which comprise a wound-contacting portion composed of carboxymethylated lyocell fibre or fabric, often used in conjunction with an adhesive backing layer to provide adhesion to an area of skin adjacent to or surrounding the wound. Such dressings have proved to be very effective in the treatment of localised wounds and are particularly superior to conventional dressings composed of fibrous gauzes and waddings for use with moist or exuding wounds. However, their usefulness is limited in respect of large-scale wounds (such as extensive burns) and in fragile areas (such as may be associated with cancerous or fungating wounds), where the use of adhesive attachment means is difficult. Dressing retention can also be a problem in awkwardly shaped parts of the body such as armpits.

It is also known to provide wound dressings composed of certain materials in the form of a garment or an inflexible three-dimensional shape complementary to the shape of a body part. For example, GB 2,357,286 discloses a process for preparing a shaped polyurethane article for use as or in a wound dressing, for example a glove dressing for a whole hand, in which a last having the desired three-dimensional shape is provided, an aqueous layer is applied over the last, a layer of an isocyanate-capped prepolymer is applied over the last to react with the aqueous layer and form a polyurethane foam layer, which is then stripped from the last. Also, U.S. Pat. No. 5,437,621 discloses a medical dressing for covering a wound, for example in the shape of a glove, comprising material having at least three layers, namely an innermost layer comprising a porous polyethylene film which enables moisture to be wicked away from the injury, a middle layer comprising an absorbent material for absorbing the moisture from the innermost layer, and an outer layer comprising a flexible, waterproof and breathable material. Other body-shaped wound dressings are disclosed in EP 0,769,283 and WO86/04811.

To the best of our knowledge, however, it has not previously been suggested to provide body-shaped wound dressings incorporating a carboxymethylated cellulosic fabric. This may well be because it can be difficult to create a body-shaped wound dressing from carboxymethylated cellulosic fibre because of the inherent weakness of such fibre, which may preclude normal knitting into body-shaped format such as gloves, and because of the need to keep the fibre dry during processing to stop it absorbing moisture and becoming sticky.

The present invention therefore seeks to provide improved wound dressings in the form of body-shaped components having a wound-contacting surface and methods of manufacturing them.

DISCLOSURE OF THE INVENTION

We have found that improved wound dressings in the form of a body-shaped component, such as a garment or part of a garment, having a wound-contacting surface are composed of carboxymethylated cellulose fabric, especially fabric which has been carboxymethylated at least at the wound-contacting surface after provision in body-shaped form. Such dressings are particularly suitable for use on moist or exuding wounds that are either extensive or otherwise difficult to treat with conventional dressings. The body-shaped dressings have a three-dimensional shape as opposed to being flat, albeit they are flexible or deformable. Their shape is such that when placed on a body part they are able to remain there of their own accord and do not fall off without the aid of an adhesive layer, although it is not necessary for them to have a tight fit with the body part for which they are designed.

The invention provides a method of manufacturing a wound dressing in the form of a body-shaped component, characterised in that the wound dressing is composed of carboxymethylated cellulosic fabric and has been obtained by a method comprising the steps of forming a body-shaped component comprising a cellulosic material and subjecting said body-shaped component to a carboxymethylation process to carboxymethylate the cellulosic material at the surface which in use of the dressing contacts a wound.

Cellulosic fabrics which have not been carboxymethylated are stronger than the corresponding carboxymethylated cellulosic fabrics. Thus, they may be formed into body-shaped components by a wide variety of methods in any manner convenient.

A number of advantages stem from the provision of a carboxymethylated cellulose wound dressing in the form of a garment or other body-shaped component. Most importantly, the dressing may literally be tailor-made to suit the particular size and shape of the wounded body part to be treated. For example, a dressing for an extensively wounded hand or a wounded finger may be provided in the form of a glove or a finger stall; a dressing for an infant suffering widespread burns may be provided in the form of a baby's body suit; and a dressing for wounds to the upper torso may be provided in the form of a vest or T-shirt. Numerous further examples of suitably shaped dressings for specific purposes (e.g. tubes, socks, balaclavas, whole head or face masks, underpants, etc)

will immediately suggest themselves to those skilled in the art. The dressings can therefore posess the flexibility and other desirable advantages of cellulosic textile material.

The inherent gel-forming characteristic of carboxymethylated cellulosic materials may be turned to particular advantage in dressings according to the invention, since gel formation on the surface of the body-shaped component which is destined to come into contact with the skin of the patient in the vicinity of the wound will greatly ease the manner in which the body-shaped component may be slid over the wounded area of the body and mininmise the pain associated with this operation. Thus, for example, the internal surface of a dressing according to the invention (for example a glove) may be sprayed with water or saline solution before being applied to the patient.

Because of the inherent weakness and moisture sensitivity of carboxymethylated cellulose it can be very difficult to construct a body-shaped component from already carboxymethylated fabric or from fabric produced from already carboxymethylated fibres. According to the method of the invention the wound dressings are manufactured by subjecting finished garments or other body-shaped components of cellulosic material which is not carboxymethylated to a carboxymethylation process after formation of the garment or other body-shaped component. Indeed, a further significant advantage of the invention is that there is a ready supply of garments or other body-shaped components suitable for conversion into dressings according to the invention, since virtually any body-shaped component made of cellulosic fabric (for example cotton, or a manmade cellulosic substance such as lyocell) may be used. Such materials can essentially be purchased "off the shelf".

The body-shaped component need not be composed exclusively of cellulosic material but may be made of a mixture of different cellulosic fibres and/or of mixtures of cellulosic with non-cellulosic fibres, provided that an appropriate degree of carboxymethylation is achieved. If a mixture of cellulosic and non-cellulosic fibres is to be subjected to carboxymethylation any non-cellulosic fibres should be able to withstand the carboxymethylation conditions. The body-shaped component optionally includes a yarn with elastic properties such as Lycra or other spandex yarn. This will assist it to assume the shape of the wearer once applied.

The body-shaped component can incorporate one or more medicaments. For example, an antimicrobial agent, or an antibiotic, or an anaesthetic, or an anti-inflammatory agent, or a skin protective agent, or a substance intended to negate malodours, can be incorporated. Suitable antimicrobial agents include silver or silver-containing compounds, povidone iodine and formulations which release hydrogen peroxide.

The incorporation of a medicament can be achieved in a variety of ways. For example, silver or other metal ions can be chemically bound by ion-exchange reactions. Other medicaments might be added during the last stage of, or in an additional stage following, the carboxymethylation process by contacting a solution of the medicament with the body-shaped component which is then dried, leaving a deposit of the medicament on the surface of the body-shaped component.

In some preferred embodiments, the body-shaped component is one piece of fabric, for example manufactured by a continuous knitting process. Alternatively, the body-shaped component may be constructed from two or more pieces of fabric sewn or otherwise fastened together, in which case care should be taken to ensure that the pieces are fastened together by means, such as a suitable sewing yarn (for example nylon yarn), that is not degraded by the carboxymethylation process.

Where the garment is tubular or encompassing, it can be provided with a zone of weakness or a removable connector such as a pull-thread acting like a rip-cord, so that the garment can be opened up and peeled off for removal. It could also be formed with suitable connectors, such as hook and loop connectors, for example Velcro (™), to assist removal of the wound dressing.

Carboxymethylation may be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art; they may, for example, be identical or similar to those described in WO93/12275, WO94/16746 or WO00/01425, the contents of which are incorporated by reference herein and to which the reader is directed for further detail.

Desirably, the carboxymethylation is carried out in the presence of industrial methylated spirits (IMS), and IMS is preferably also used in a subsequent washing step, suitably along with water, as a cleaner and steriliser. Such a method of subjecting the finished body-shaped component to the carboxymethylation process has the added advantage of producing a sterile or near-sterile product as a result of cleaning with the IMS/water mixture. It may therefore be unnecessary to provide a further sterilisation step as would be unavoidable if an attempt were to be made to produce the body-shaped component from cellulosic material which had already been carboxymethylated. Contaminants such as grease, dirt and germs picked up during formation are removed and/or sterilised during the IMS cleaning step. The resulting carboxymethylated body-shaped component can then be packaged and further sterilised in a sealed package by various methods such as gamma irradiation.

The degree of carboxymethylation is desirably such that, upon absorption of moisture, the fibres at the skin-contacting surface of the body-shaped component form a gel but preferably the fabric retains sufficient fibrous character that the body-shaped component retains its integrity during application to, use on and removal from the patient. The cellulosic material may be carboxymethylated only at the wound-contacting surface, or cellulosic material remoter from that surface may also be carboxymethylated; for example the cellulosic material may be carboxymethylated throughout.

The invention is hereinafter described in further detail, by way of example only, with reference to the following Example carried out using a commercially available body suit composed of 100% cotton and weighing 62 g for a baby.

EXAMPLE 23.7 g of NaOH was added to 64.0 g of water and stirred with a glass rod to obtain a homogeneous solution. In a separate beaker, 35.6 g of sodium monochloroacetate (SMCA) was added to 79.9 g of water and stirred to obtain a homogeneous solution. The solutions were then mixed and 162.1 g of industrial methylated spirit (IMS) added. The reactants were stirred quickly and the body suit was immersed in the mixture. The reaction vessel was then sealed and placed in a water bath at 73° C. for 95 minutes. During the reaction, the flask was opened every 10 minutes to agitate the liquors physically and to turn over the body suit to ensure even contact with the liquors.

After the treatment, the reaction mixture was neutralised with 43 ml glacial acetic acid for 10 min at 73° C. Two wash stages were then carried out, each at 70° C. for 10 min. Wash liquors were made up of 189.3 g IMS, 145 g water and 2.0 g citric acid. Tween 20 (a softening agent) was then applied as the finish at 73° C. using 301 g IMS, 34.2 g water and 2.0 g Tween 20 (polysorbate 20). During the wash and neutralisation stages, agitation was carried out using a glass rod. Finally, excess liquors were squeezed out by hand and the body suit dried in an oven at 50° C. for 2 hours.

When tested, the body suit was subjected to a subjective "gel feel" test. A satisfactory degree of slipperiness was detected, indicating successful carboxymethylation.

The invention claimed is:

1. A method of manufacturing a wound dressing in the form of a body-shaped component, wherein the wound dressing is composed of carboxymethylated cellulosic fabric and has been obtained by a method comprising the steps of forming a body-shaped component comprising a cellulosic material and subjecting said body-shaped component to a carboxymethylation process to carboxymethylate the cellulosic material at the surface which in use of the dressing contacts a wound, the carboxymethylated body-shaped component having a three dimensional shape as opposed to being flat, its shape being such that when placed on a body part it is able to remain there of its own accord and does not fall off without the aid of an adhesive layer.

2. The method according to claim 1, wherein the fabric comprising a cellulosic material is a woven, non-woven or knitted fabric composed of fibres of a natural cellulosic substance or of a man-made cellulosic substance or of a mixture of such substances.

3. The method according to claim 2, wherein the fabric comprising a cellulosic material is composed of cotton or of lyocell or a mixture thereof.

4. The method according to claim 1, wherein the carboxymethylation process comprises the steps of treating the fabric, either sequentially or simultaneously, with sodium hydroxide and monochloroacetic acid or a salt thereof in the presence of industrial methylated spirits and subjecting the resulting material to a washing step with industrial methylated spirits.

5. the method according to claim 1, wherein the body-shaped component is in the form of a garment or part thereof.

6. The method according to claim 1, wherein the cellulosic material includes fibres and the carboxymethylation process is carried out to provide a degree of carboxymethylation such that, upon absorption of moisture, the fibres at the surface of the body-shaped component which in use of the wound dressing contact a wound form a gel but the fabric retains sufficient fibrous character so that the body-shaped component retains its integrity during application to, use on and removal from the wound.

7. The method according to claim 1, wherein the carboxymethylation process is carried out to carboxymethylate the cellulosic material not only at the surface which in use of the dressing contacts a wound but also to carboxymethylate the cellulosic material remote from that surface.

8. The method according to claim 1, wherein the body-shaped component is composed of a single piece of fabric.

9. The method according to claim 1, wherein the body-shaped component is composed of at least two pieces of fabric sewn together with a yarn composed of a material that is not degraded by the carboxymethylation process.

10. The method according to claim 1, wherein the fabric comprising a cellulosic material also contains non-cellulosic fibre.

11. The method according to claim 10, wherein the fabric includes a non-cellulosic yarn with elastic properties.

12. The method according to claim 1, wherein it includes the step of providing the dressing with a removable connector.

13. The method according to claim 12, wherein the removable connector is a pull thread.

* * * * *